United States Patent
Jonsson

(10) Patent No.: US 6,648,499 B2
(45) Date of Patent: Nov. 18, 2003

(54) METHOD AND DEVICE FOR EXTRUDING BONE CEMENT UNDER VACUUM

(75) Inventor: Soren Jonsson, Linkoping (SE)

(73) Assignee: Cemvac System AB, Linkoping (SE)

( * ) Notice: Subject to any disclaimer, the term of this patent is extended or adjusted under 35 U.S.C. 154(b) by 0 days.

(21) Appl. No.: 09/881,540

(22) Filed: Jun. 14, 2001

(65) Prior Publication Data

US 2002/0191485 A1 Dec. 19, 2002

(30) Foreign Application Priority Data

Jun. 14, 2001 (WO) ................................ PCT/SE01/01345

(51) Int. Cl.⁷ .................................................. B01F 13/06
(52) U.S. Cl. ...................................................... 366/139
(58) Field of Search ................................. 366/130, 139, 366/189, 242, 244–247, 255–256, 332, 333; 206/219, 221; 222/325–327, 386, 386.5

(56) References Cited

U.S. PATENT DOCUMENTS

| | | |
|---|---|---|
| 1,211,426 A | 1/1917 | Farrington |
| 3,036,819 A | 5/1962 | Peterson |
| 4,463,875 A | 8/1984 | Tepic |
| 4,671,263 A * | 6/1987 | Draenert |
| 4,676,406 A | 6/1987 | Frischmann et al. |
| 4,721,390 A * | 1/1988 | Lidgren |
| 4,758,096 A * | 7/1988 | Gunnarsson |
| 4,966,601 A | 10/1990 | Draenert |
| 5,100,241 A | 3/1992 | Chan |
| 5,193,907 A | 3/1993 | Faccioli et al. |
| 5,252,301 A | 10/1993 | Nilson et al. |
| 5,328,262 A | 7/1994 | Lidgren et al. |
| 5,549,380 A | 8/1996 | Lidgren et al. |
| 5,549,381 A * | 8/1996 | Hays et al. |
| 5,551,778 A * | 9/1996 | Hauke et al. |
| 5,624,184 A * | 4/1997 | Chan |
| 5,779,356 A | 7/1998 | Chan |
| 5,797,678 A | 8/1998 | Murray |
| 5,934,803 A | 8/1999 | Hutter |
| 6,017,349 A | 1/2000 | Heller et al. |
| 6,042,262 A | 3/2000 | Hajianpour |
| 6,120,174 A | 9/2000 | Hoag et al. |
| 6,176,607 B1 | 1/2001 | Hajianpour |
| 6,312,149 B1 | 11/2001 | Sjovall et al. |
| 6,406,175 B1 * | 6/2002 | Marino |

FOREIGN PATENT DOCUMENTS

| | | |
|---|---|---|
| JP | 6-100056 | 4/1994 |
| SE | 510490 | 5/1999 |
| WO | 87/05492 * | 9/1987 |
| WO | WO 93/22041 | 11/1993 |
| WO | WO 94/05415 | 3/1994 |
| WO | WO 94/26403 | 11/1994 |
| WO | WO 97/18031 | 5/1997 |
| WO | 99/67015 | 12/1999 |

* cited by examiner

Primary Examiner—Charles E. Cooley
(74) Attorney, Agent, or Firm—Merchant & Gould, P.C.

(57) ABSTRACT

A method and a device for preparation of bone cement. The constituent components of bone cement are mixed under vacuum in a closed mixing chamber, which has a vacuum connection (4), a moveable wall section (2), a device arranged to maintain the moveable wall section (2) in its initial position during the mixing process, an extrusion opening located opposite to the moveable wall section (2) and a device (9) arranged to openably seal the extrusion opening. The extrusion is performed by the moveable wall section (2) being brought to move towards the extrusion opening, by applying a force against the moveable wall section (2) using an extrusion tool (12). The moveable wall section (2) is set free after mixing is finished and thereafter forced towards the extrusion opening for compression of bone cement while the extrusion opening is sealed by the sealing device (9).

7 Claims, 5 Drawing Sheets

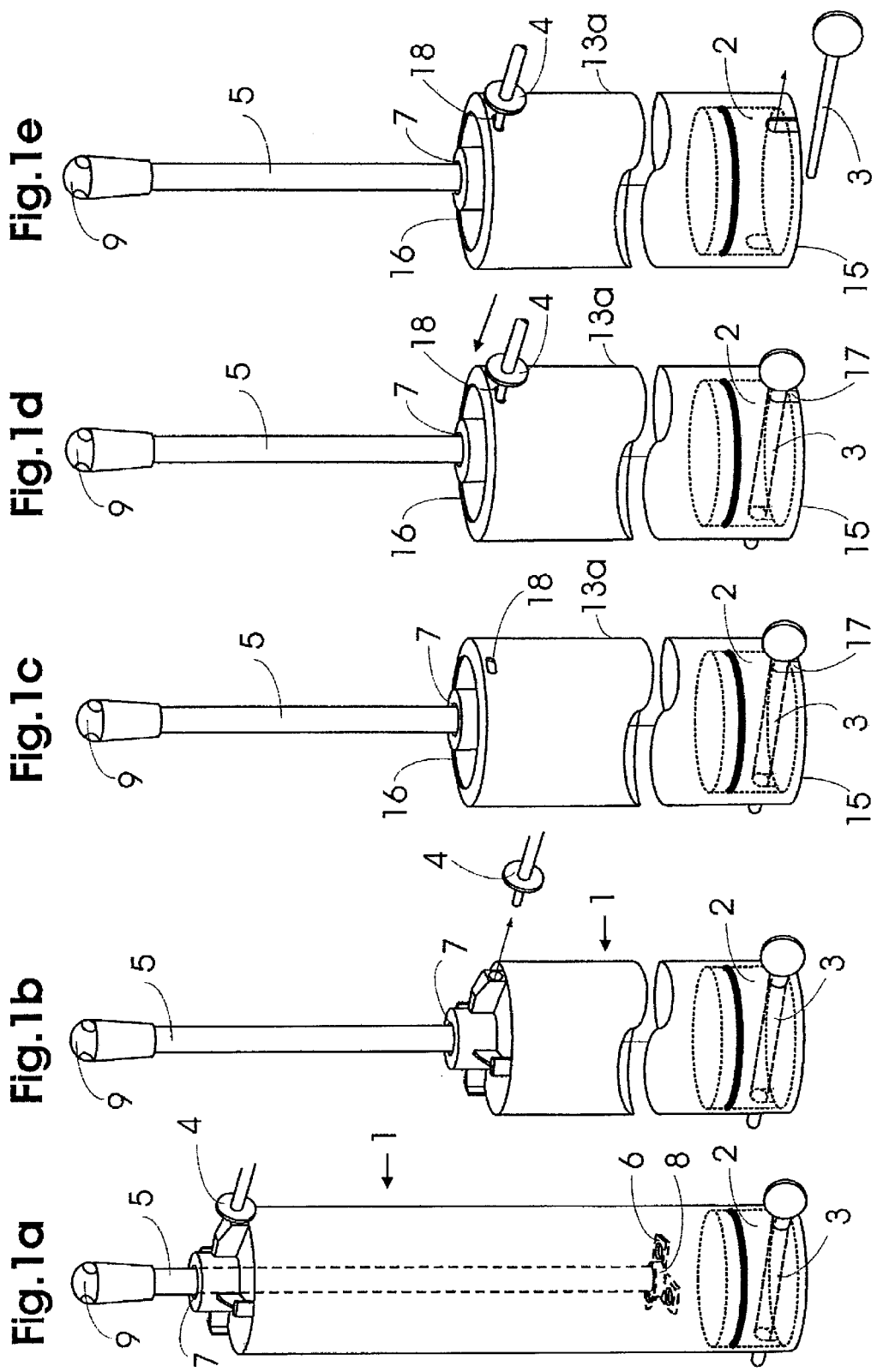

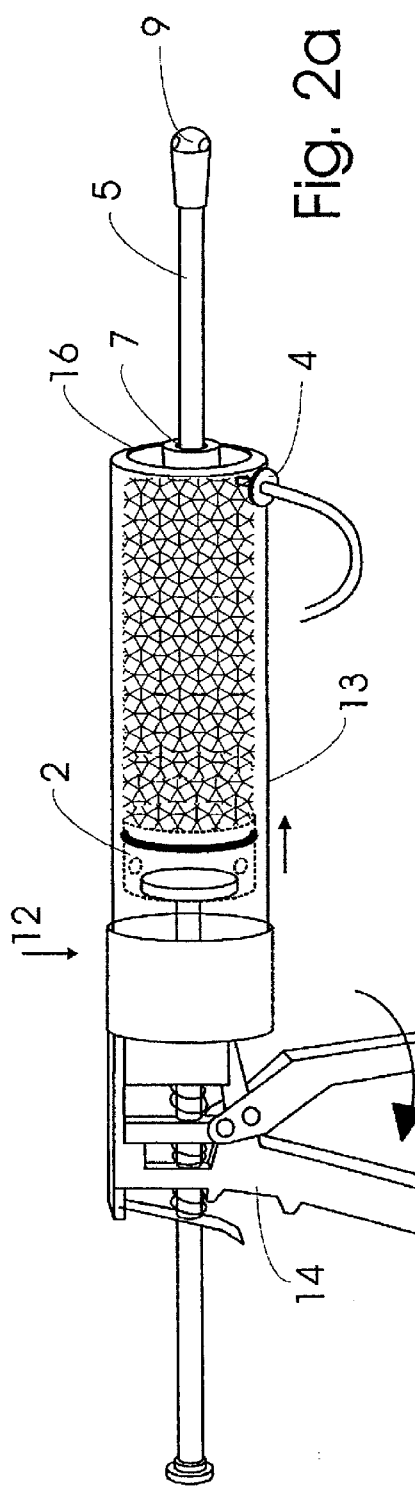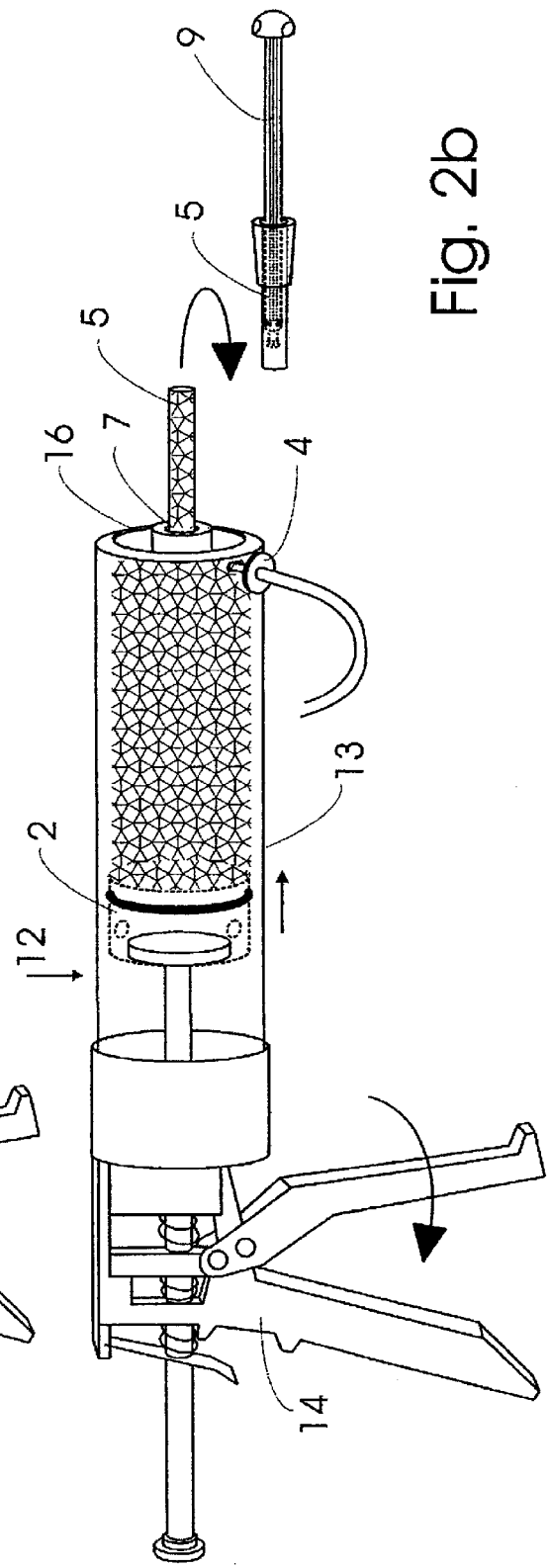

METHOD AND DEVICE FOR EXTRUDING BONE CEMENT UNDER VACUUM

BACKGROUND OF THE INVENTION

The present invention relates to a method for preparing bone cement.

The invention also relates to a device for preparing bone cement.

When preparing bone cement it is important, considering the future strength of the bone cement, to achieve a bone cement which is as free as possible from pores and the like caused by air or gas inclusions. These inclusions may be caused by remaining air and gases, occurring when mixing the components of the bone cement, which during the mixing procedure are mixed into the bone cement mass.

From SE-9200360-7 it is previously known how to collect dispersed bone cement, by means of the movement occurring under the influence of vacuum in the mixing chamber when the movable wall section is set free, to form a bone cement pillar in the evacuation section of the mixing chamber. To prevent air, to the extent possible, from leaking in one or several O-rings are arranged around the movable wall section. The O-rings will cause an increased friction implying that the movement of the movable section as well as the collection of bone cement thereby will be poor or prevented when the sealing causes too high friction. Consequently it can be stated, for known devices or methods for preparation of bone cement, that it must be accepted to allow some air or gas inclusions.

SUMMARY OF THE INVENTION

The object of the present invention is to produce improved removal of air and gas inclusions in the bone cement. In addition assurance is attained that the movable wall section always will be moved and that thereby improved collection of bone cement is obtained.

In one aspect of the invention, a method for preparing bone cement is provided. The constituent components of the bone cement are mixed under vacuum in a closed mixing chamber which is formed with a moveable wall section that is fixed during the mixing process. After mixing is finished, extrusion of bone cement is performed by releasing the moveable wall section and bringing the moveable wall section towards an extrusion opening. As the moveable wall section is brought towards the extrusion opening, the bone cement is compressed.

In another aspect of the invention, a device for preparing bone cement is provided. The device includes a mixing chamber equipped with a vacuum connection, a wall section that is movable in the direction of the opposite part of the mixing chamber, and a device arranged to maintain the moveable wall section in its initial position during the mixing process. An extrusion opening is located opposite to the moveable wall section of the mixing chamber and a sealing device is arranged to openably seal the extrusion opening. Further, an extrusion tool is arranged to apply a force towards the moveable wall section to perform the extrusion. Prior to extrusion, the extrusion opening is sealed by the sealing device for compression of the bone cement.

BRIEF DESCRIPTION OF THE DRAWINGS

In the following the invention will be explained in more detail by means of examples of embodiments of the present invention and with reference to the accompanying drawings.

FIG. 1a illustrates a mixing chamber, in accordance with the invention, during mixing of the constituent components of bone cement.

FIGS. 1b–1e illustrate a number of phases when the mixing chamber is introduced into a sleeve of an extrusion tool.

FIG. 2a and FIG. 2b illustrate how the compression and extrusion procedures respectively are carried out by means of the extrusion tool.

DESCRIPTION OF THE INVENTION

Figure 3:
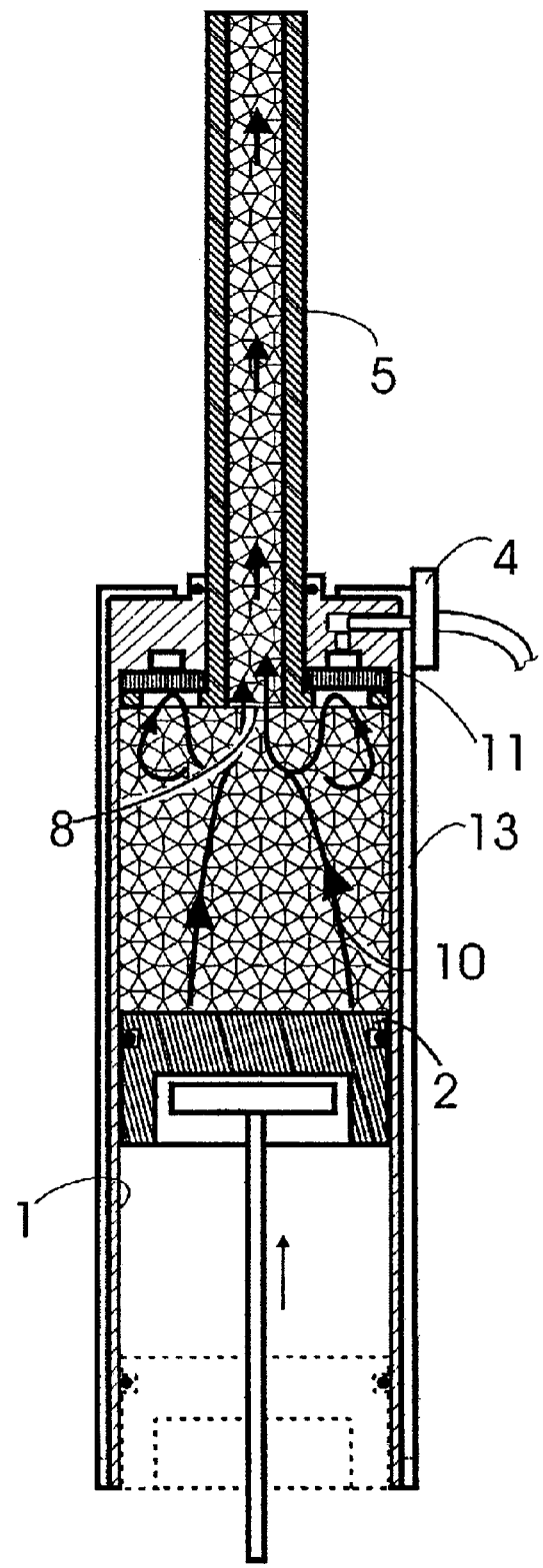
FIG. 3 illustrates the movement of the bone cement in the mixing chamber during the extrusion process.

In the drawing designation 1 indicates a mixing chamber and 2 a moveable wall section, which is detachably fixed in its initial position by means of a locking pin 3. The mixing chamber 1 is equipped with a vacuum connection 4 and an agitator device. The agitator device comprises of an agitator rod 5 with an axial extrusion channel for bone cement and an agitator 6 arranged around the end of agitator rod 5 within mixing chamber 1. The agitator rod 5 and the mixing chamber 1 are for reasons, which will be apparent later, preferably made from a transparent material.

The agitator rod 5 is axially moveable in mixing chamber 1 through opening 7 which is sealed against agitator rod 5. The orifice of the channel of agitator rod 5, in mixing chamber 1, forms an extrusion opening 8 for bone cement at agitator 6. During mixing a sealing rod 9 is inserted into the channel of agitator rod 5 to seal extrusion opening 8. Flow line 10 illustrates the path of the bone cement during compression and extrusion processes at which the bone cement passes a filter 11 arranged in connection with vacuum connection 4.

The device according to the invention also comprises an extrusion tool 12 with a sleeve 13a and an extrusion pistol 14. Sleeve 13a is formed with an opening 15 for introduction of mixing chamber 1, an opening 16 for agitator rod 5, two grooves 17 for locking pin 3 and an opening 18 for vacuum connection 4.

Mixing chamber 1 is, when preparing bone cement, used to mix the constituent cement components under vacuum. The bone cement components are introduced into mixing chamber 1 after which agitator rod 5 of the agitator device, is axially moved in and out of mixing chamber 1, and preferably turned at the same time through opening 7. The actual mixing is performed by agitator 6, arranged around the end of agitator rod 5 within mixing chamber 1, since it is turned and moved among the bone cement components by means of the previously mentioned movement of agitator rod 5. During the entire mixing process extrusion opening 8 in association with the agitator 6 will come into contact with the bone cement. Leakage of bone cement out of and air into mixing chamber 1 via extrusion opening 8 is prevented during mixing by sealing rod 9.

When it is established that the bone cement components are sufficiently mixed the device is prepared for bone cement extrusion. The agitator rod 5 is then moved out of mixing chamber 1 as far as possible at which agitator 6 and extrusion opening 8 connect to the wall, located opposite to the moveable wall section 2 of mixing chamber 1. The extrusion process, wherein the bone cement is moved out of mixing chamber 1 through extrusion opening 8 and into the channel of agitator rod 5 functioning thereby as a nozzle, may then start.

Compression of the bone cement is, according to the present invention, performed before extrusion. The object with the compression is to squeeze remaining air and gas inclusions out of said bone cement to achieve as compact a material as possible. Both compression and extrusion are performed by means of extrusion tool 12, which is similar to a spray pistol for sealing compounds or similar, and sleeve 13a, in which mixing chamber 1 is placed after finished mixing.

Mixing chamber 1 is inserted into sleeve 13a through opening 15 and placed inside sleeve 13a such that agitator rod 5, when completely pulled out, is sticking out of sleeve 13a through opening 16. Sleeve 13a is formed with grooves 17 to keep locking pin 3, and thus the movable wall section 2, in its initial position during the insertion. The side wall of sleeve 13a is formed such that vacuum connection 4 has to be removed before insertion. However, opening 18 allows for reconnection of vacuum connection 4 after insertion. The phases in relation to insertion of mixing chamber 1 into sleeve 13a are illustrated in FIGS. 1b–e.

When mixing chamber 1 is placed inside sleeve 13a of extrusion tool 12, vacuum connection 4 is reconnected and the moveable wall section is set free by means of the locking pin 3 being removed. These phases are illustrated in FIGS. 1d–e. The extrusion pistol 14 of extrusion tool 12 is thereafter connected to sleeve 13a and the actual compression of the bone cement may start.

The compression, which also is performed under vacuum, is executed by a force applied by means of extrusion pistol 14, against the moveable wall section 2 such that it is moved towards extrusion opening 8. The bone cement will then move along the flow lines 10, illustrated in FIG. 3, and be compressed towards extrusion opening 8. Passing towards extrusion opening 8 the bone cement will come into contact with filter 11 while air and gas inclusions are exhausted by suction through vacuum connection 4. After compression to a certain degree the bone cement will push sealing rod 9, which seals extrusion opening 8, ahead of the bone cement and out of the channel of agitator rod 5, in which bone cement in the shape of a column is formed. When desired length of the bone cement column is obtained, agitator rod 5 is cut off at the front of the obtained bone cement column just at or ahead of the sealing rod 9. The extrusion and application of the bone cement may then be performed. FIGS. 2a and 2b illustrate the compression and extrusion processes while mixing chamber 1 is placed inside sleeve 13a and connected to extrusion pistol 14.

Figure 4:
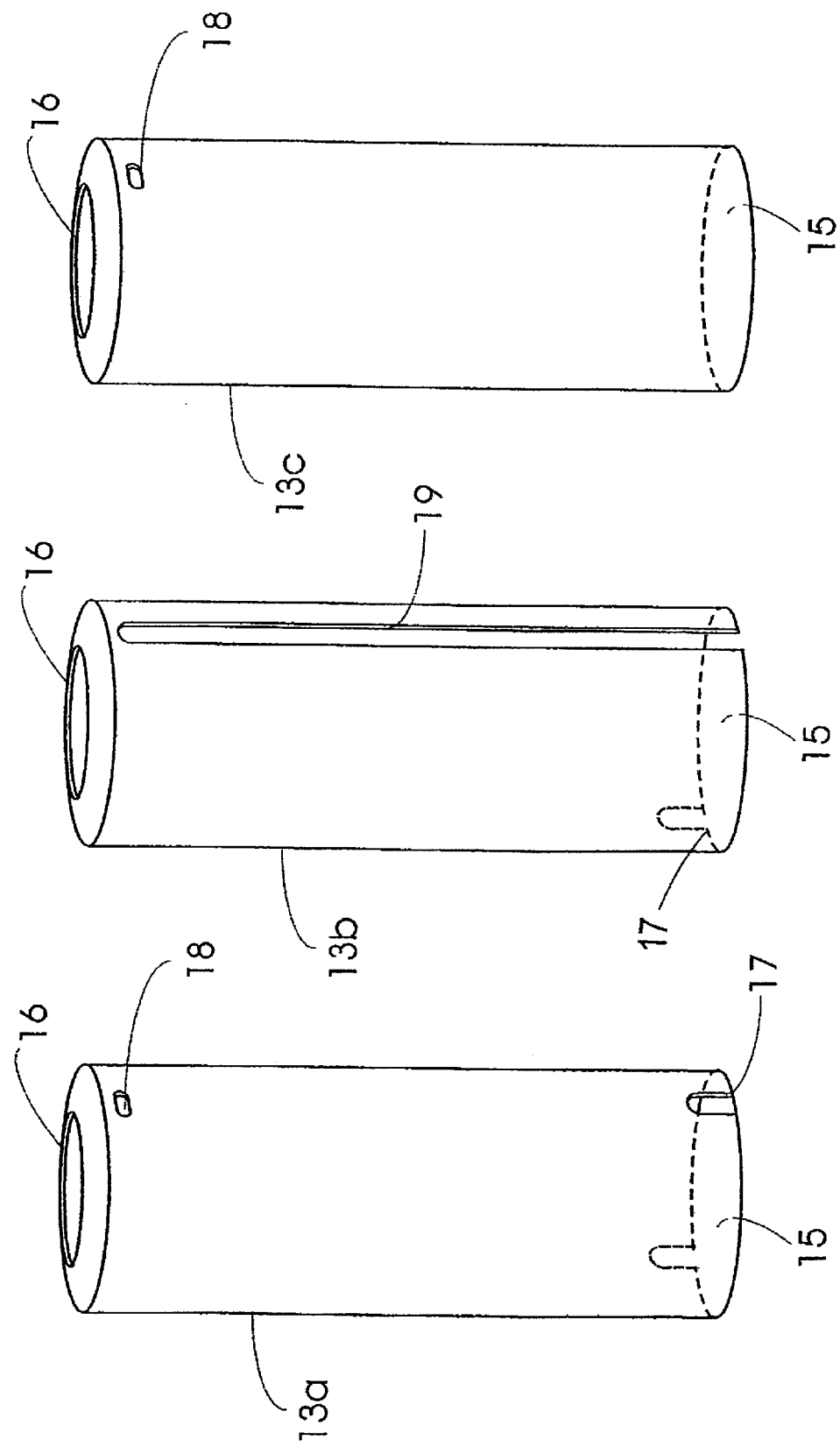
FIGS. 4a–4c illustrate three different embodiments, according to the invention, of a sleeve integral with said extrusion tool.

The present invention also comprises two alternative embodiments, 13b and 13c, of the sleeve of extrusion tool 12, these are illustrated in FIGS. 4b and 4c.

Figure 5:
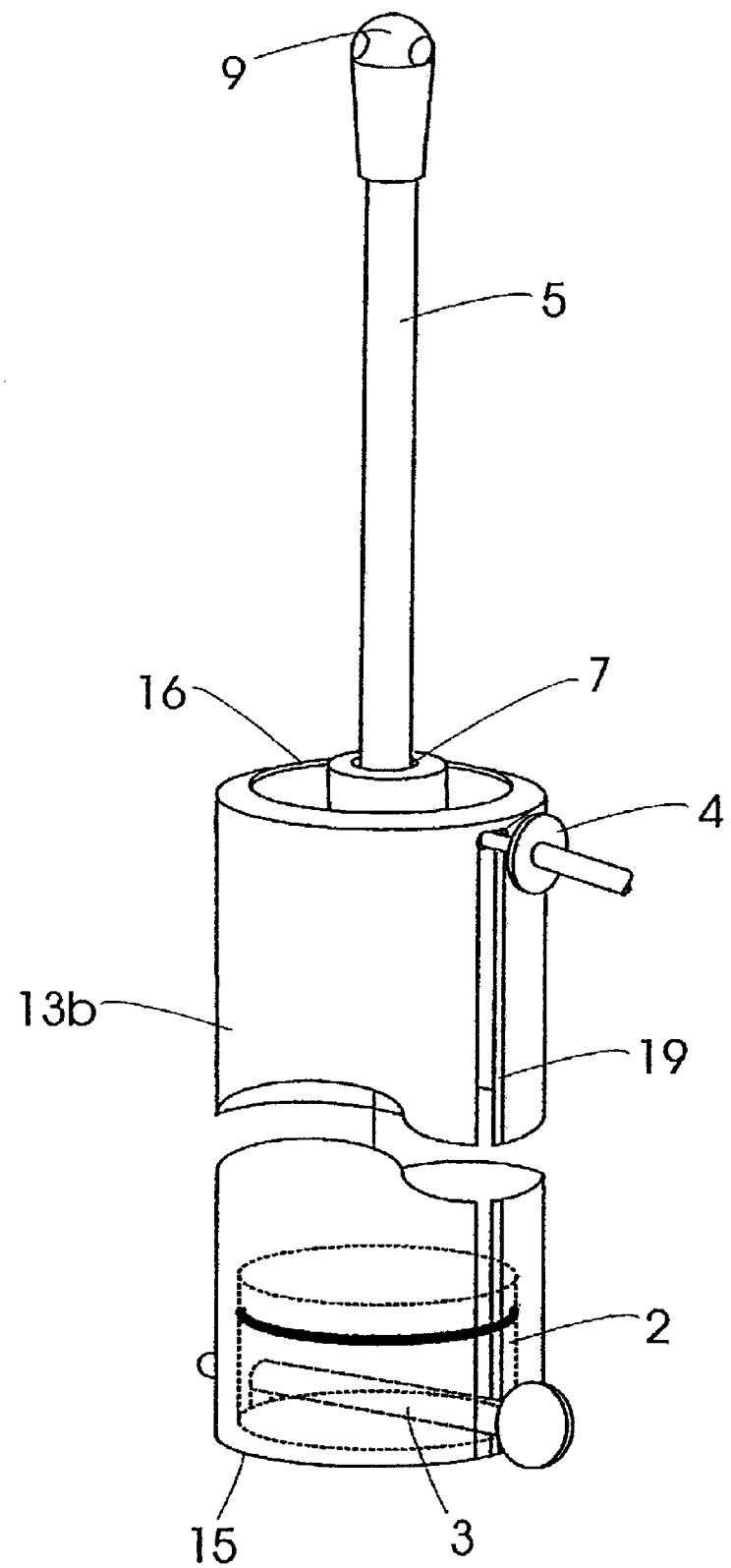
FIG. 5 illustrates the mixing chamber introduced into an alternative embodiment of the sleeve designed with a cutout.

In the sidewall of sleeve 13b a groove 17 and a cut-out 19 are formed. The cut-out 19 extends along most of the wall of sleeve 13b, with the aim to prevent the vacuum connection 4 from having to be removed before the insertion of mixing chamber 1. The vacuum connection 4 may thereby be kept during mixing, subsequent compression and extrusion processes, which are similar to the process described in relation to sleeve 13a. Furthermore the cut-out 19 and the groove 17 imply that the locking pin 3 may be kept during the insertion too. FIG. 5 illustrates the mixing chamber 1 inserted into sleeve 13b.

Sleeve 13c is formed without any groove or cut-out in the side wall, which means that this sleeve is used when both vacuum connection 4 and locking pin 3 are removed before the insertion of mixing chamber 1. However, sleeve 13c is formed with an opening 18 in order to allow vacuum connection 4 to be reconnected prior to subsequent compression and extrusion processes, which are performed in the same way as when sleeve 13a or 13b is used.

Common factors for the three sleeves 13a–c according to the invention, are that their interior is formed such that it is adjusted to the form of mixing chamber 1, this by having opening 15 for insertion of mixing chamber 1 and opening 16 for agitator rod 5, and that anyone of them may be used for an extrusion process performed under vacuum. However, the three sleeves 13a–c differ from each other in whether they allow vacuum connection 4 and locking pin 3 to be kept in place during insertion of the mixing chamber 1, which will result in differing influences on the moveable wall section 2 in the process after insertion.

A negative pressure will arise in the mixing chamber 1 when the vacuum connection 4 is connected. This implies that the moveable wall section 2 will be influenced by the vacuum so that the wall section 2 tends to be sucked into the mixing chamber 1. If the moveable wall section 2 is set free when vacuum connection 4 is connected, which is the case at reconnection of the vacuum connection 4 after insertion of the mixing chamber 1 into sleeve 13c, the moveable wall section 2 will be sucked into the mixing chamber 1. When the mixing chamber 1 is placed in sleeve 13a or 13b the moveable wall section 2 is, despite the influence of the vacuum, kept in its initial position by the locking pin 3 and can therefore not be moved before removing locking pin 3.

It is apparent, for anyone skilled in the art, that the present invention is not restricted to the above-described embodiments. For example extrusion may also be performed by means of an extrusion tool assuming other embodiments than mentioned above.

What is claimed is:

1. A method for preparation of bone cement, comprising:
providing a closed mixing chamber having a detachably fixed wall section that is moveable within the chamber and an extrusion opening;
mixing constituent components of bone cement under vacuum in the mixing chamber to form bone cement; and
extruding the bone cement from the mixing chamber by actuating the wall section toward the extrusion opening, wherein the extruding of the bone cement is performed under maintained vacuum in the mixing chamber.

2. A method for preparation of bone cement, comprising:
providing a closed mixing chamber having a detachably fixed wall section that is moveable within the chamber, an extrusion nozzle defining an extrusion opening, and a sealing device arranged within the extrusion nozzle and sealing the extrusion opening;
mixing constituent components of bone cement under vacuum in the mixing chamber to form bone cement;
compressing the bone cement in the mixing chamber by actuating the wall section toward the extrusion opening with the sealing device arranged in the extrusion nozzle, wherein during compression the sealing device is forced partially out of the extrusion nozzle by a column of bone cement that is formed in the extrusion nozzle;
terminating compression after a desired length of the column of bone cement is formed; and cutting the extrusion nozzle off just ahead of the front of the column of bone cement.

3. The method of claim 2, wherein the compression of the bone cement is performed under maintained vacuum in the mixing chamber.

4. A device for preparing and extruding bone cement, comprising:

a mixing chamber equipped with a vacuum connection for connection to a vacuum source, the mixing chamber having an extrusion opening and a moveable wall section within the mixing chamber and moveable toward the extrusion opening;

a device configured and arranged to maintain the moveable wall section at an initial POSITION during mixing of bone cement constituents in the mixing chamber;

a sealing device configured and arranged to seal the extrusion opening; and an extrusion tool that includes a sleeve that is configured and arranged to receive the mixing chamber, and a mechanism that is configured and arranged to apply an actuating force to the moveable wall section to perform extrusion, and wherein the sleeve is configured and arranged to allow the connection between the vacuum source and the vacuum connection to be maintained during extrusion of the bone cement.

5. The device of claim 4, wherein the sleeve has two grooves formed therein that are configured and arranged to enable the device to keep the moveable wall section at its initial position during insertion of the mixing chamber into the sleeve, and the sleeve further includes an opening that allows the vacuum source to be reconnected to the vacuum connection after insertion.

6. The device of claim 4, wherein the sleeve has a cut-out that is configured and arranged to enable the connection between the vacuum connection and the vacuum source to be maintained during insertion of the mixing chamber into the sleeve, and the sleeve includes a groove that is configured and arranged to enable the device to keep the moveable wall section at its initial position during insertion of the mixing chamber into the sleeve.

7. The device of claim 4, wherein the sleeve includes an opening that allows the vacuum source to be reconnected to the vacuum connection after insertion of the mixing chamber into the sleeve.

* * * * *